US011445975B2

United States Patent
Nikolic (10) Patent No.: US 11,445,975 B2
(45) Date of Patent: Sep. 20, 2022

(54) METHODS AND SYSTEMS FOR IMPROVED PREDICTION OF FLUID RESPONSIVENESS

(71) Applicant: CN MEDICAL RESEARCH LLC, New Orleans, LA (US)

(72) Inventor: Cvetko Nikolic, New Orleans, LA (US)

(73) Assignee: CN MEDICAL RESEARCH LLC, New Orleans, LA (US)

(*) Notice: Subject to any disclaimer, the term of this patent is extended or adjusted under 35 U.S.C. 154(b) by 178 days.

(21) Appl. No.: 16/160,778

(22) Filed: Oct. 15, 2018

(65) Prior Publication Data

US 2019/0046113 A1 Feb. 14, 2019

Related U.S. Application Data

(63) Continuation-in-part of application No. 15/221,128, filed on Jul. 27, 2016.
(Continued)

(51) Int. Cl.
*A61B 5/00* (2006.01)
*G06K 9/62* (2022.01)
(Continued)

(52) U.S. Cl.
CPC ............ *A61B 5/4848* (2013.01); *A61B 5/352* (2021.01); *A61B 5/366* (2021.01); *A61B 5/4839* (2013.01);
(Continued)

(58) Field of Classification Search
None
See application file for complete search history.

(56) References Cited

U.S. PATENT DOCUMENTS

| 5,339,818 A | * | 8/1994 | Baker | ............... A61B 5/02156 600/490 |
| 7,422,562 B2 | | 9/2008 | Hatib et al. | |

(Continued)

FOREIGN PATENT DOCUMENTS

WO 2017100188 A2 6/2017

OTHER PUBLICATIONS

Zheng et al. "ECG Based Identification by Deep Learning", Oct. 20, 2017, International Conference on Financial Cryptography and Data Security; Springer, Berlin, Heidelberg, pp. 503-510.
(Continued)

*Primary Examiner* — Jacqueline Cheng
*Assistant Examiner* — Jairo H Portillo
(74) *Attorney, Agent, or Firm* — FisherBroyles, LLP; Jason P. Mueller (57) ABSTRACT

The present disclosure provides systems and methods for predicting fluid responsiveness. Embodiments include sensors configured to obtain a high-resolution electrocardiogram signal and a computer system connected to the sensors that detects and processes changes in at least one of length, amplitude, slope, area, depth, and height of at least one of P, Q, R, S, T, and U complex of the electrocardiogram signal caused by the influence of physiological variables on each other to create a prognostic index. The prognostic index of the changes in the electrocardiogram signal may then be used to generate a fluid responsiveness prediction. The fluid responsiveness prediction may then be used to control fluid administration for patients that are receiving anesthesia during surgery or that are critically ill or unresponsive. Disclosed embodiments may also be used as a diagnostic tool for athletes during training, who are undergoing endurance tests, for bike riders, etc.

18 Claims, 2 Drawing Sheets

Related U.S. Application Data (60) Provisional application No. 62/197,429, filed on Jul. 27, 2015.

(51) Int. Cl.

| | | |
|---|---|---|
| *G06K 9/00* | (2022.01) | |
| *G16H 50/30* | (2018.01) | |
| *G16H 40/63* | (2018.01) | |
| *A61B 5/352* | (2021.01) | |
| *A61B 5/366* | (2021.01) | |
| *G06V 10/44* | (2022.01) | |
| *G06V 30/194* | (2022.01) | |
| *A61B 5/029* | (2006.01) | |

(52) U.S. Cl.
CPC ........ *A61B 5/7267* (2013.01); *G06K 9/00536* (2013.01); *G06K 9/6223* (2013.01); *G06K 9/6227* (2013.01); *G06K 9/6271* (2013.01); *G06K 9/6297* (2013.01); *G06V 10/454* (2022.01); *G06V 30/194* (2022.01); *G16H 40/63* (2018.01); *G16H 50/30* (2018.01); *A61B 5/029* (2013.01); *A61B 5/4821* (2013.01); *A61B 2503/10* (2013.01)

(56) References Cited

U.S. PATENT DOCUMENTS

| | | |
|---|---|---|
| 8,265,739 B1 | 9/2012 | Boileau et al. |
| 8,617,135 B2 | 12/2013 | Rinehart et al. |
| 8,790,272 B2 | 7/2014 | Sackner et al. |
| 2004/0199482 A1* | 10/2004 | Wilson ............ A61B 5/7267 706/25 |
| 2005/0004481 A1* | 1/2005 | Xue ............... A61B 5/349 600/509 |
| 2010/0324827 A1 | 12/2010 | Addison et al. |
| 2011/0270111 A1 | 11/2011 | Cannesson |
| 2012/0035442 A1 | 2/2012 | Barman et al. |
| 2012/0179011 A1 | 7/2012 | Moon et al. |
| 2012/0310050 A1* | 12/2012 | Osorio ............. A61B 5/1118 600/300 |
| 2013/0053664 A1* | 2/2013 | Jian ............... A61B 5/0205 600/324 |
| 2013/0085357 A1 | 4/2013 | Huber et al. |
| 2014/0012148 A1 | 1/2014 | Amit et al. |
| 2014/0058229 A1 | 2/2014 | Su et al. |
| 2014/0187992 A1 | 7/2014 | Wilmering |
| 2014/0213862 A1 | 7/2014 | Addison et al. |
| 2014/0316278 A1* | 10/2014 | Addison ............ A61B 5/7278 600/476 |
| 2015/0257690 A1 | 9/2015 | Su et al. |
| 2017/0112401 A1 | 4/2017 | Rapin et al. |

OTHER PUBLICATIONS

Mathews et al. "A novel application of deep learning for single-lead ECG classification", Computers in Biology and Medicine, New York, US, vol. 99, Jun. 4, 2018, pp. 53-62.

Sbrollini et al. "Serial electrocardiography to detect newly emerging or aggravating cardiac pathology: a deep-learning approach", BioMedical Engineering OnLine, Feb. 12, 2019, issue 18, article 15. https://biomedical-engineering-online.biomedcentral.com/articles/10.1186/s12938-019-0630-9.

* cited by examiner

METHODS AND SYSTEMS FOR IMPROVED PREDICTION OF FLUID RESPONSIVENESS

This application is a continuation-in-part of U.S. patent application Ser. No. 15/221,128 filed Jul. 27, 2016, which claims the benefit of U.S. Provisional Patent Application No. 62/197,429, filed Jul. 27, 2015. The disclosure of each of these applications is incorporated herein by reference.

DESCRIPTION OF EMBODIMENTS

An important issue for physicians in the treatment of patients that are receiving anesthesia during surgery or that are critically ill or unresponsive to interventions is determining how much, if any, intravenous fluid or blood should be administered to the patient in order to maintain optimal cardiac output. Indeed, determining the best and correct course of fluid therapy for a patient is very difficult and clinicians have very few clinical signs to direct them on the right path.

Fluid administration in a hemodynamically unstable patient constitutes a major challenge when it comes to measuring hemodynamic parameters in real time. Accurate clinical assessment of hypovolemia (a state of decreased blood volume) is difficult, as is the decision to undertake fluid resuscitation as the initial treatment strategy. Specifically, predicting whether a hemodynamically unstable patient will positively respond to fluid therapy with an increase in stroke volume and cardiac output is very difficult. On one hand, an insufficient supply of fluid or blood volume can cause a suboptimal (i.e., reduced) cardiac output, which will in turn lead to hypoperfusion, insufficient tissue perfusion, and eventually, organ failure and/or dysfunction. On the other hand, recent studies have shown that an oversupply of fluid or blood volume may also lead to pulmonary or cardiac failure, extended ventilation time, and/or disruption of the endothelial layer of the vascular system with consecutive blood clotting and passage of fluid into the interstitium (edema). Further, an increased supply of fluid or blood volume does not provide any benefit to patients with decreased heart frequency or contractility; instead, these patients may need heart muscle strengthening medication (such as catecholamines, adrenaline, or their derivatives). A patient's "fluid responsiveness" is thus considered the most important determinant to assess the adequacy of fluid administration and in ensuring optimal cardiac performance and organ perfusion.

Therefore, under conditions of physiological compromise, it has become extremely important to adjust the fluid supply to the exact level required to keep the heart functioning in its optimal range of operation [stroke volume× heart frequency/minute=cardiac output]. Further, the heart's response to this fluid supply, i.e., the heart's "fluid responsiveness", must be continuously monitored to maintain heart function within optimal ranges.

Treatment of the anaesthetized or critically ill patient requires an accurate assessment of the patient's intravascular volume status ("cardiac preload") and the likelihood that the patient will respond (through increased "stroke volume") to a fluid challenge ("fluid responsiveness"). Stroke volume is the amount of blood ejected by the left ventricle of the heart in one contraction. The left ventricle of the heart fills with blood until contraction during diastole (also known as the end diastolic volume, or EDV). The contraction occurs during systole, and some blood is left in the ventricle after contraction (also known as the end systolic volume, or ESV). Stroke volume is then calculated as the difference of ESV from EDV. Stroke volume is then divided by EDV to determine the ejection fraction, or EF. Typical ranges of EF in healthy subjects are between 55-70%. Stroke volume is also affected by preload and afterload. Preload is the load, or stretch, put on the ventricle by the amount of entering blood volume. As preload increases, it increases the strength of the contraction, thus increasing the stroke volume. The afterload is the resistance the ventricle must pump against to eject the stroke volume.

The primary reason to give a patient a fluid challenge is to increase the stroke volume (fluid responsiveness). If the fluid challenge does not increase the stroke volume, volume loading serves the patient no useful benefit (and in fact may be harmful). According to the Frank-Starling principle, as the preload increases, left ventricular (LV) stroke volume increases until the optimal preload is achieved at which point the stroke volume remains relatively constant. In normal physiologic conditions, both ventricles should operate on the ascending portion of the Frank-Starling (FS) curve. In most people, in the ascending portion of the FS curve, an increase in preload (with volume challenge) will result in a significant increase in stroke volume.

A number of methods and techniques have been developed to predict whether and how much fluid should be administered or supplied to a patient in order to maintain optimal heart operation. A method that has been demonstrated to be a useful predictor of fluid responsiveness is the use of Stroke Volume Variations ("SVV"), which are variations observed in the left ventricular stroke volume that result from the interaction of the cardiovascular system and the lungs under mechanical ventilation. SVVs are caused by the cyclic increases and decreases in the intrathoracic pressure due to mechanical ventilation, which lead to variations in the cardiac preload and afterload. Another method that has been demonstrated to be a useful predictor of fluid responsiveness is the use of Pulse Pressure Variations (PPV), which are respiratory variations in arterial blood pressure. However, both of these methods have several disadvantages, including that they require at least some level of invasiveness (e.g. arterial line to assess blood pressure)—a drawback because the general trend in this field has been towards less invasiveness, i.e., providing interventions and monitoring to patients correlating to the sensitivity of their state. For example, patients who undergo fluid increases (for example, ICU patients) are typically in a sensitive state, and so should receive treatment that is less invasive (and yet optimally invasive for their sensitive state) compared to a relatively healthier patient. Specifically, an increased intrathoracic pressure like in the case of mechanical ventilation (for example, during anesthesia or in the ICU) can obstruct the backflow of blood to the heart (for a couple of heartbeats). This effect may be even more pronounced when a higher pressure is applied to a patient with poor blood circulation (potentially causing demasking/hypovolemia).

Further, current methods for predicting "fluid responsiveness" involve a single parameter based on one or more of: a derivative of the pulse curve from an arterial measurement, a direct measurement of the stroke volume (surface area integral), and a measurement of blood flow velocity in the AoK (DOPPLER Principle). However, these methods have several limitations, including that they are not sufficiently accurate because they are based on a single parameter and do not necessarily account for the different changes caused by the influence of physiologic variables on each other. Additionally, these currently known methods for determination of the "fluid responsiveness" parameter are almost all derivatives of blood flow.

Methods and systems are provided for fluid responsiveness, and, in particular though non-limiting embodiments, methods and systems are provided for predicting fluid responsiveness using an electrocardiogram signal to maintain optimal cardiac output.

Embodiments of the present disclosure predict fluid responsiveness using the value of an electrocardiogram (ECG or EKG) signal alone and perform this function at higher ECG sampling rates. Importantly, the present disclosure is completely non-invasive and does not disturb the patient in any way because its function derives from the standard functional analysis of an ECG signal. ECG is a graphical representation of the electric potentials generated by the heart. It is a non-invasive and continuous monitoring method providing information from which the heart rate, underlying rhythm, activity of the atria, and the ventricles can be read in the form of an electrical signal. Such electrical signals are recorded via ECG leads placed on the surface of a body. The ECG has been exclusively used until this point as a monitoring process to monitor heart frequency and arrhythmias in anesthesiology and intensive care medicine.

An exemplary embodiment of the present disclosure predicts fluid responsiveness by using continuous, higher resolution ECGs (e.g., 250 Hz to 1000 Hz) to detect changes in fluid responsiveness parameters. Unlike standard ECGs at 50 Hz, a higher resolution ECG can detect very low amplitude signals in the ventricles (called "Late Potentials") of patients with abnormal heart conditions.

Embodiments of the present disclosure are also not based on a single parameter, but on an algorithm based on changes in an ECG signal caused by the influence of multiple physiologic variables (heart rate, breathing, vascular tone, etc.) on each other—thus providing the necessary accuracy not possible from analyzing a single parameter.

The present disclosure provides systems and methods for predicting fluid responsiveness using a cardiac parameter from an ECG signal to maintain optimal cardiac output. Specifically, the disclosed embodiments present a method for predicting fluid responsiveness by using continuous, higher resolution ECGs (ranging from 250 Hz to preferably 1000 Hz) to detect and process changes in fluid responsiveness parameters based on the ECG signals and generate a fluid responsiveness prediction based on those changes. In alternative embodiments, fluid responsiveness may be predicted using non-continuous or partially continuous higher resolution ECGs.

In an embodiment of the present disclosure, at least two sensors may be provided to obtain an ECG signal non-invasively. The ECG signal may be passed from the sensors to a computer system by various methods, including via an electronic output file. A processor within the computer system may be configured to detect and process changes in the ECG signal fluid responsiveness parameters (i.e. direct alterations of the ECG curves). Once these changes in the ECG signal are processed, the processor may execute a mathematical algorithm stored within a memory of the computer system to analyze and quantify the changes in the ECG signal and generate a fluid responsiveness prediction. A display device may also be provided to display the results of the fluid responsiveness prediction.

According to exemplary embodiments of the present disclosure, methods are provided for predicting fluid responsiveness of a patient using an ECG signal. A method includes obtaining the ECG signal non-invasively using a sensor. The method includes processing changes in the ECG signal fluid responsiveness parameters (i.e. direct alterations of the ECG curves) using a computer system. The method includes quantifying these changes in fluid responsiveness parameters and generating a fluid responsiveness prediction of a patient using a mathematical algorithm embodied within the computer system. The method includes displaying the results of this fluid responsiveness prediction to a physician or other health care provider using a display device. The method may also include a physician or other health care provider using his or her medical expertise and evaluating the results of this fluid responsiveness prediction and determining the next appropriate medical course of action for the patient. This next medical course of action may include, but is not limited to, administering fluid or medication to the patient, performing other medically appropriate steps as necessary based on the results of the fluid responsiveness prediction, or do nothing at all, if medically appropriate.

Figure 1:
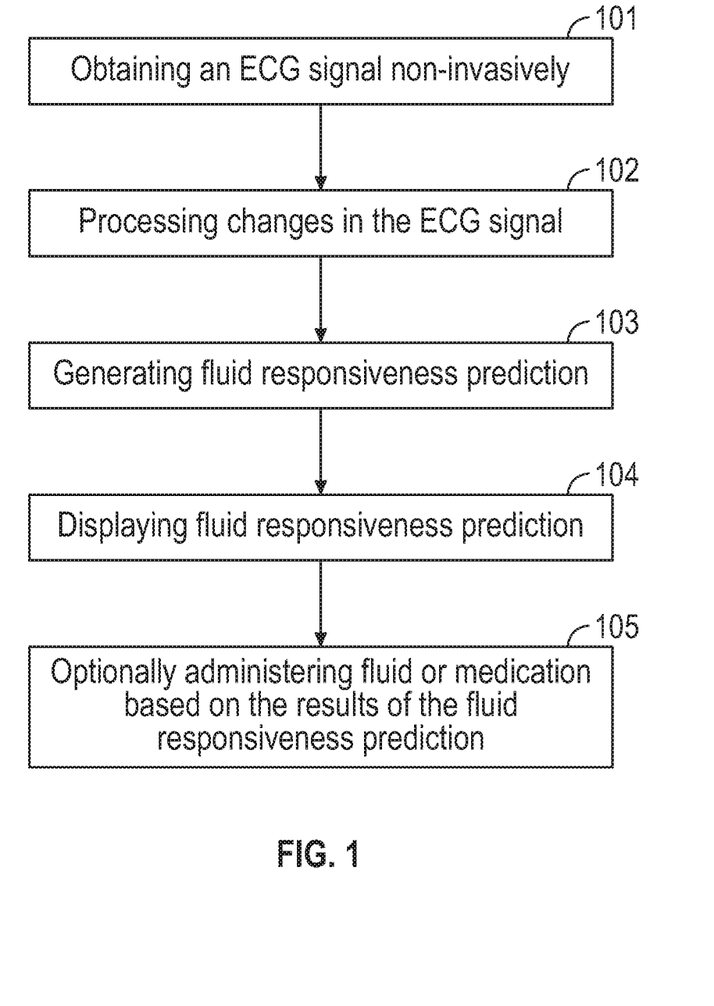
FIG. 1 is a flow chart of a method of predicting fluid responsiveness of a patient using an ECG signal, according to an exemplary embodiment of the present disclosure.

FIG. 1 illustrates of a method of predicting fluid responsiveness of a patient using an ECG signal to maintain optimal cardiac output of the patient, according to an exemplary embodiment of the present disclosure. The first step may include obtaining an ECG signal from a patient non-invasively 101. The second step may include processing changes in the ECG signal 102. The third step may include generating a fluid responsiveness prediction 103. The fourth step may include displaying the fluid responsiveness prediction 104 to a physician or other health care provider. Finally, the optional fifth step may include administrating fluid or medication based on the results of the fluid responsiveness prediction 105. Although embodiments of the present disclosure describe methods of predicting fluid responsiveness using an ECG signal, alternative embodiments may use any recordable physiological (electrical) signal, including Electromyogram (EMG) signals, Electroencephalogram (EEG) signals, etc.

Figure 2:
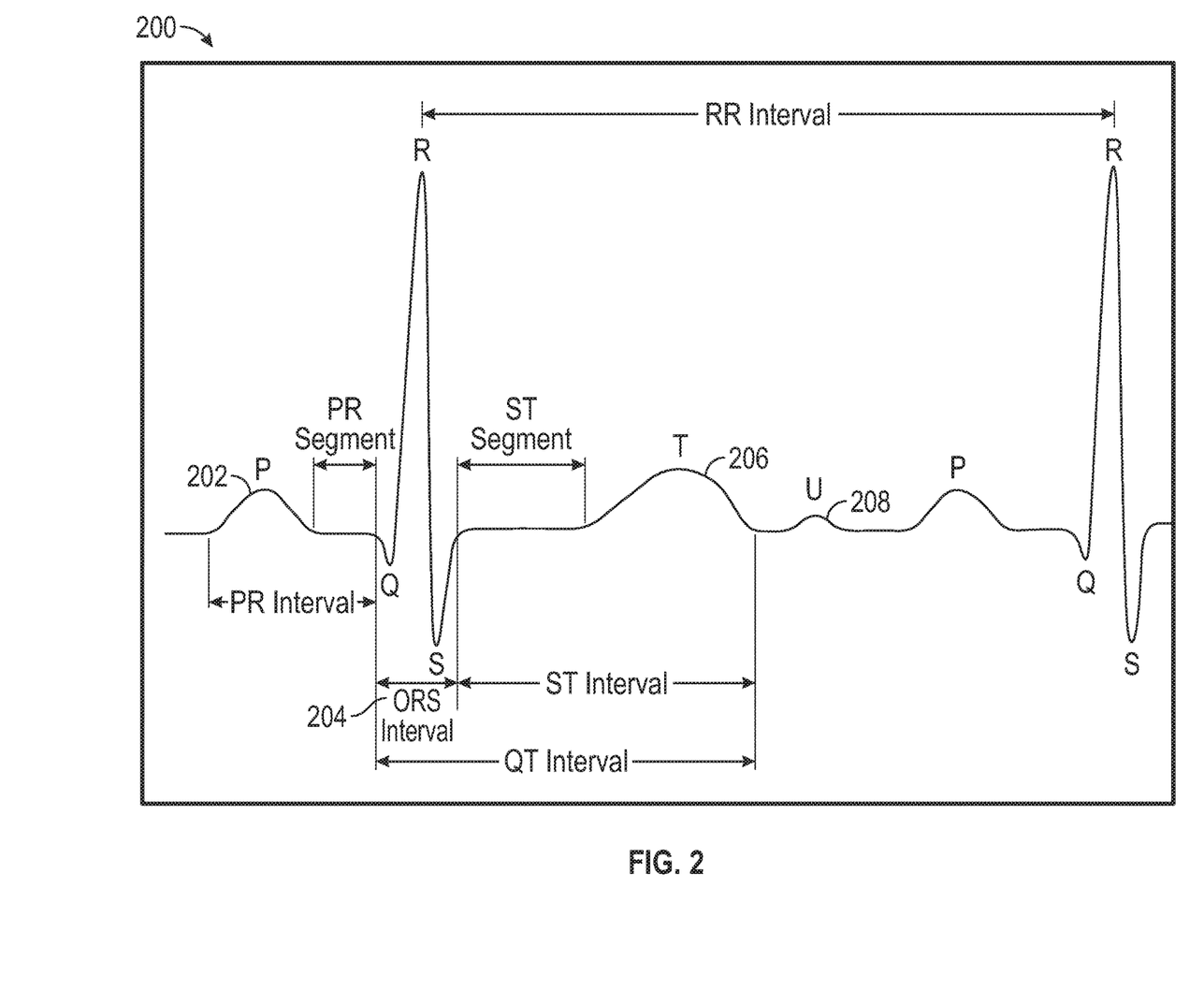
FIG. 2 illustrates a typical ECG signal over a time interval.

FIG. 2 illustrates a typical ECG signal 200 over a time interval. Electrocardiography represents a transthoracic (across the thorax or chest) measurement of electrical activity of the heart over a period of time, as detected by electrodes attached to the outer surface of the skin and recorded by a device external to the body. The recording produced by the noninvasive procedure is termed EKG or ECG. An ECG is used to measure the rate and regularity of heartbeats, as well as the size and position of the chambers, the presence of any damage to the heart, and the effects of drugs or devices used to regulate the heart, such as a pacemaker.

In FIG. 2, an ECG signal 200 is shown. The ECG signal 200 includes a P wave 202, a QRS complex 204, a T wave 206, and a U wave 208. The P wave 202 indicates atrial depolarization, or contraction of the atrium. The QRS complex 204 indicates ventricular depolarization, or contraction of the ventricles. The T wave 206 indicates ventricular repolarization. The U wave 208 typically follows the T wave 206 and may not always be seen. U wave 208 may indicate repolarization of the papillary muscles or Purkinje fibers. The size of the U wave 208 is inversely proportional to the heart rate; as the U wave 208 grows bigger, the heart rate slows down.

Turning back to FIG. 1, each step of the method of predicting fluid responsiveness of a patient will now be addressed in turn. Referring to the first step of obtaining an ECG signal from a patient non-invasively 101, the term non-invasively indicates that no artificial methods are used during the recording of the ECG signal to create an increased intrathoracic pressure. Artificial methods may include any measurements that may, for example, puncture the surface of a patient's skin to obtain an ECG signal. Artificial methods do not include, for example, mechanical ventilation or leg raising of a patient that may be performed to improve the quality of the measurements being obtained. In some embodiments, the ECG signal may be obtained from at least two sensors coupled to a patient. A sensor may be a device capable of generating continuous, high-resolution ECG data (e.g., 250 Hz to 1000 Hz). Examples of such devices include commercially available ECG setups from GE Healthcare® Inc. In an alternative embodiment of the present disclosure, the ECG signal may be passed from the sensors to a storage device, whereby the ECG signal may be obtained from the storage device. A storage device may be an apparatus capable of providing continuous, high-resolution ECG data (e.g., 250 Hz to 1000 Hz). Embodiments of the storage device include a flash memory or hard disk drive. Exemplary embodiments of the present disclosure may use continuous, high-resolution ECGs (ranging from at least 250 Hz to preferably 1000 Hz) to facilitate the fluid responsiveness prediction. Although the disclosed embodiments refer to a sensor and storage device, the ECG signal may be acquired from other known types of ECG acquisition hardware.

In an embodiment of the present disclosure, the ECG signal may be passed from the sensors or the storage device to a computer system. Passing the ECG signal to the computer system may be done in various ways, including via an electronic output file (and/or related ECG acquisition hardware). In further embodiments, sensors may be configured to communicate with the computer system through wireless channels. For example, sensors may communicate using Bluetooth, near-field, WiFi, or other wireless communication protocols. Sensors may be lightweight, compact, and portable. In some embodiments, sensors may be configured to be worn by a patient (or test subject) and to measure ECG signals of the person wearing the sensor. Wearable sensors may be configured to be worn on a person's wrist, arm, leg, strapped around the person's chest, etc. In further embodiments, may other types of sensors may be used to measure ECG signals and to provide such ECG signals to a computer system using available wired or wireless technology.

In exemplary embodiments, the computer system may be a device, apparatus, and system capable of processing continuous, high-resolution ECG data (e.g., 250 Hz to 1000 Hz). Embodiments of the computer system include commercially available desktop computer systems such as a PowerMac®. The computer system may include a general-purpose control unit, such as a processor or microprocessor connected to an internal bus, data acquisition, data storage, and/or input/output devices including a display device and printer. The processor or microprocessor may be configured to execute software, which may include an operating system and one or more applications, as part of performing the functions described herein. A read-only memory (ROM), a random access memory (RAM), user inputs, and a display device may also be operatively connected to the bus.

The RAM and the ROM are illustrated by way of example, and not limitation. Any suitable computer-readable media may be used in the system for data storage. Computer-readable media are configured to store information that may be interpreted by the microprocessor. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

Referring now to the second step of processing changes in the ECG signal 102, a processor within the computer system may detect, analyze, and process changes in the fluid responsiveness parameters (i.e., direct alterations of the ECG curves) to create a prognostic index. Particularly, the processor may be configured to detect and process changes in at least one of the length, amplitude, slope, area, depth, and height of at least one of the P, Q, R, S, T, and U complex (see FIG. 2) of the ECG signal caused by the influence of various physiological variables on each other to create the prognostic index. This prognostic index may be based on processed changes in the ECG signal fluid responsiveness parameters caused by the influence of at least two or more physiological variables on each other such as heart rate, breathing, and/or vascular tone. The changes in the ECG signal may be detected in volume depleted patients comparing ECG periods during the end of inflation of a ventilator hub and during the end of the exhalation period (i.e., during periods of differing intrathoracic pressures). An alternative embodiment of the present disclosure may involve the use of methods and systems of the present disclosure in spontaneous breathing patients.

Specifically, the prognostic index (and subsequently generated fluid responsiveness prediction) may be based on several relative changes in at least one of the P, Q, R, S, T, and U complexes of the ECG curve, including, but not limited to, at least one of the absolute length of the P wave/10-25%, the absolute amplitude of the P wave/10-30%, the slope of the P wave/5-25%, the area under the curve of the P wave/10-30%, the PQ segment/15-35%, the absolute length of the QRS complex, the slope of the decrease from isoelectric to the Q point, the slope of the increase towards the R point, the absolute depth of the Q point, the absolute height of the R point, the area under the curve of the QRS complex, the absolute length of the ST segment, the absolute length of the ST segment including the T wave, the absolute length of the ST segment including the U wave, the distance from the beginning of the P wave and the top of the P wave to the top of R, the slope of the distance from the beginning of the P wave and the top of the P wave to the top of R, the distance from the top of R to the end of the T wave, the slope of the distance from the top of R to the end of the T wave, and/or the area under the triangle built of both the distance from the beginning of the P wave and the top of the P wave to the top of R, as well as its corresponding slope, with an isoelectric line (e.g., see FIG. 2). In some embodiments, if more than one ECG signals are used, the fluid responsiveness prediction may be based on the change in vector, change of a heart's electrical axis of the respective ECG leads. All of these changes in the P, Q, R, S, and T complexes of the ECG curve may be observed in fluid responsive patients in a digital overlay of ECG curves comparing a curve during end of inflation (ventilator hub) to end of exhalation. Further, all of these changes may be within a range of 10-30%—the more volume depleted (fluid responsive) a patient is, the higher the difference in his or her corresponding intra-thoracic pressure.

The above referenced changes in the P, Q, R, S, T, and U complexes of the ECG curve does not have to be observed in one patient; in fact, the more these changes are observed and compared in several individual patients during ventilation and the more pronounced they are, the more certain the fluid responsiveness prediction. In various embodiments, the prognostic index may include data derived from observations and comparisons of changes in multiple patients. Particularly, the larger the number of empirical data points present, i.e. the larger the number of patients evaluated, the more comparative data may be obtained. Further, the longer the empirical data points are recorded/collected from individual patients, the more comparative data may be obtained. In some embodiments, the prognostic index may therefore include both existing data collected based on changes in the P, Q, R, S, T, and U complexes of high-resolution ECG signals in multiple patients, and/or newly collected data based on the same changes from an individual patient. The existing data may act as a baseline to which the newly collected data may be compared. In other embodiments, the prognostic index may only include newly collected data from an individual patient. In this embodiment, varying information within the newly collected data may be analyzed and compared to each other. Therefore, embodiments of the present method may include using a high-resolution ECG device to generate a prognosis based on comparing changes in at least one of the P, Q, R, S, T, and U complexes of high-resolution ECG signals relative to a pre-determined prognostic index based on data collected from multiple patients, or relative to each other based on data collected from an individual patient.

Embodiments of the present disclosure may employ various methods for detecting, analyzing, and processing the changes in at least one of the P, Q, R, S, T, and U complexes of multiple ECG signals. In an exemplary embodiment, this analysis may be based on a mathematical integration known as the "Simpson's rule" or modifications thereof such as, e.g., the "Composite Simpson's rule." In numerical analysis, the Simpson's rule is a method for numerical integration, the numerical approximation of definite integrals. If the function being integrated is relatively smooth over a time interval, the Simpson's rule may be used to obtain an adequate estimated approximation of underlying data to the exact integral. However, when trying to integrate numerical data that is not smooth over a time interval (as may be the case for the data in the prognostic index described herein), the Simpson's rule may not be as accurate. However, by breaking up the interval into a number of small subintervals, the Simpson's rule may then be applied to each subinterval, with the results being summed to produce an approximation for the integral over the entire interval. In particular embodiments, this modified application of the Simpson's rule (i.e., the Composite Simpson's rule) may therefore be used to perform analysis and quantification of the data in the prognostic index. In alternative embodiments, other suitable methods of analysis may be used to analyze the data in the prognostic index.

Referring now to the third step of generating a fluid responsiveness prediction 103, the processor may execute a mathematical algorithm stored within a memory of the computer system to analyze, quantify, and combine the prognostic index of the changes in the ECG signal and generate a fluid responsiveness prediction based on numerical data in the prognostic index. Particularly, the fluid responsiveness prediction may be obtained based on an analysis and comparison of existing and newly collected data in the prognostic index. In some embodiments, the fluid responsiveness prediction may be generated by analyzing and comparing data obtained from one data set (i.e. from one patient being evaluated) to an established data set in the prognostic index (i.e. from multiple patients). In alternative embodiments, the fluid responsiveness prediction may be generated by analyzing and comparing changes in fluid responsiveness in an individual patient. For example, in an embodiment, data being collected from a patient may indicate certain ECG curves with relatively higher "spikes"/"peaks" than other ECG curves of the same patient or other patients based on existing data in the index. These spikes may be evaluated and characterized as numerical data via the methods of analysis described herein. A fluid responsiveness prediction comparing the newly collected and existing data may then be generated and displayed in various forms, including but not limited to as a table, listing, chart, and/or other suitable visual depictions such as a digital overlay of ECG curves.

Referring now to the fourth step of displaying the fluid responsiveness prediction 104 to a healthcare provider or other authorized person, the generated fluid responsiveness prediction may be displayed on a display device communicatively coupled to the computer system. The display device may be a cathode ray tube display, a flat panel display, such as a liquid crystal display (LCD), a light-emitting diode (LED) display, a plasma display, or other type of monitor. Embodiments of the display device include commercially available monitors, such as an Apple Thunderbolt Display. It will be understood that other suitable metrics may be displayed to indicate levels of fluid responsiveness, such as by a status bar, a visual alarm, an audible alarm, any other suitable indication, or combinations thereof. The level of fluid responsiveness may also be outputted to suitable output devices, such as a computer, a computer-readable medium, a printer, or combinations thereof.

An exemplary embodiment of the disclosure may further include the optional fifth step whereby a physician or other health care provider may review the results of the generated fluid response prediction on the display device and make the medical determination to administer fluid to a patient 105. An alternative exemplary embodiment of the disclosure may include the optional fifth step whereby the physician or other health care provider reviews the results of the generated fluid response prediction on the display device and instead makes the determination to administer medication to the patient 105. This scenario will likely arise in a case where an increased supply of fluid or blood volume may not provide any benefit to a patient with decreased heart frequency or contractility; instead, the patient may need heart muscle strengthening medication (such as catecholamines, adrenaline, or their derivatives).

An alternative exemplary embodiment of the disclosure may include the optional fifth step whereby the physician or other health care provider may review the results of the generated fluid response prediction on the display device and instead make the determination, based on his or her expertise, to follow another medically appropriate course of action for the patient 105. Yet another exemplary embodiment of the disclosure may include a scenario whereby the health care provider or other authorized person may review the results of the generated fluid response prediction on the display device and come to the conclusion that the patient does not need any additional medical treatment at all 105.

In one exemplary but non-limiting embodiment, a hemodynamically unstable patient's fluid responsiveness may be obtained by the following method. At least two sensors described herein may first be coupled to the patient and used to obtain the patient's ECG signal (e.g., see FIG. 2). The ECG signal may be passed from the sensors to a computer system described herein. A processor within the computer system may then detect, analyze, and process changes in at least one of the length, amplitude, slope, area, depth, and height of at least one of the P, Q, R, S, T, and U complex of the ECG signal caused by the influence of the patient's various physiological variables on each other to create a prognostic index described herein. In various embodiments, the patient's ECG signal may indicate some curves with a higher "spike"/"peak" than other curves. In some embodiments, the processor may analyze and compare the area under the curve of the QRS complex of the "spiked" curve with the area under the curve of the QRS complex in another non-spiked curve. This calculation and analysis of the area under the curves of the spiked and non-spiked QRS complexes may be performed using the Composite Simpson's rule described herein. Once this data is obtained and stored in the prognostic index, the processor may then generate a fluid responsiveness prediction based on this data. In this particular embodiment, the prognostic index may only include relevant newly collected data from this patient being evaluated. For example, the relevant data from the spiked curve may be processed and compared to the data from the non-spiked curve and displayed in a suitable viewable format, e.g., a comparative chart. In other embodiments, the prognostic index may include relevant newly collected data from both the patient being evaluated as well as baseline data from multiple patients for comparison to the newly collected data. A physician viewing this comparative chart may then make the medical determination to administer fluid or medication, follow an entirely different medically appropriate course of action, or not take any further action.

According to an embodiment, a machine learning algorithm may be used to generate a model for a relationship between fluid responsiveness and an ECG signal. For example, a machine learning algorithm may generate a classifier model. In this regard, a plurality of training data sets may be used to generate the model. Each data set may be processed to identify a number of features of the data. For example, each ECG signal may be analyzed to determine a plurality of features. A feature may correspond to a peak of an ECG signal and each peak may be characterized by a peak height, an area under the curve of the ECG signal for the portion of the signal corresponding to the peak, etc. Features P, Q, R, S, T, and U may be identified as features in an ECG signal, as described in greater detail above.

Each feature may be considered to define a coordinate direction in a multi-dimensional space. Then a value associated with each peak may be taken to define a coordinate in the multi-dimensional space. As such, a peak height, an area under the curve for a given peak, etc., may be used to define a coordinate in the multi-dimensional space. As such, a given ECG signal may be represented as a single point in the multi-dimensional space. For example, suppose an ECG signal is analyzed to determine characteristic values (p, q, r, s, t, u) characterizing features P, Q, R, S, T, and U, then the data may be represented by the point (p, q, r, s, t, u). In this regard, p may be the peak height or area under the curve for feature P, q may be the peak height or area under the curve for feature Q, etc. In this way, a plurality of N data sets may be reduced to a corresponding plurality of N points in the multi-dimensional space. In this example, the space would be a six dimensional space corresponding to the six features P, Q, R, S, T, and U.

A classifier may be built as follows. A set of N ECG curves may be taken as training data. Each ECG curve may be analyzed to determine the set of values (p, q, r, s, t, u) characterizing each ECG curve. The N training data sets are thus reduced to N points in the multi-dimensional space. The training data sets may then be partitioned into one or more classifications. In a binary classifier model, for example, each of the data sets may be given one of two labels (e.g., 0 and 1) that classify each point as being in one or the other classes of data. Machine learning techniques may then be used to build a model. In this regard, the model is represented mathematically as a hyperplane (i.e., a linear separator) or a hypersurface (i.e., a non-linear separator) in the multi-dimensional space that best separates the data into the two classes.

According to an embodiment, the hyperplane or hypersurface may be represented, respectively, as a linear or non-linear function in the multi-dimensional space. Once the hyperplane or hypersurface has been established it may be used to generate predictions of the model. For example, a multi-dimensional data point (e.g., a point of the form (p, q, r, s, t, u) for the example above) may be provided as input to the model. Given the established hyperplane or hypersurface, the input point may be predicted to correspond to one of the two classes that were used to define the model. In this way, a new data point (i.e., a previously un-seen data point) may be characterized as belonging to one of the two classes that were used to define the model based on its location in the multi-dimensional space relative to the hyperplane or hypersurface that defines the classifier model.

According to various embodiments, a correlation between a patient's ECG signal and fluid responsiveness may be determined. As such, a plurality of training data sets (i.e., ECG signals) may be analyzed to determine multi-dimensional coordinates (p, q, r, s, t, u). Further, each data point may be characterized as (0) fluid non-responsive, or (1) fluid responsive. A model of fluid-responsiveness may then be generated from the training data. Once the model has been built, then a responsiveness index may be defined for each new data point corresponding to new ECG signals. As such, based on the model, a patient's ECG signal may be measured and a responsiveness index may be determined based on the model.

In further embodiments, a set of training data may be divided into three or more classifications. As such, machine learning methods may be applied to define various regions in the multi-dimensional space corresponding to the three or more classification categories. As such, a model may be built to make predictions regarding new (i.e., unseen) data. The various alternatives predicted by the model may correspond to three or more classifications of treatment options for a given patient based on his/her measured ECG signal.

According to an embodiment, the above-described method may be summarized as follows. A raw ECG signal (having been taken with high frequency sampling) is provided as input and a fluid responsiveness index is generated by the model as output. For example, an ECG signal may be read from a 1000 Hz ECG device. Computational techniques may then be applied to determine a set of features from the input ECG signal, and to thereby characterize the signal in terms of coordinates in a multi-dimensional space. During the training phase, a plurality of such data points is used to generate the model. During the testing/prediction phase, a fluid responsiveness index is generated by the model based on an input ECG signal. The fluid responsiveness index may characterize whether a patient may benefit from administration of fluid/blood that would in turn cause the patient to have an increased cardiac output. An alternative treatment may be prescribed in cases in which the fluid responsiveness index predicts that a patient would not benefit from administration of fluid/blood. In such a case, a patient may benefit from heart strengthening medications, such as catecholamines, adrenaline, etc. This in this example of how embodiment methods may be employed to automatically determine a diagnosis based on a measured input signal, such as a patient's measured ECG.

The above discussion uses the notion of a classifier model for simplicity of explanation. In further embodiments, various other machine learning methods may be used. For example, machine learning models may be based on regression models, decision trees, neural networks, etc.

A. Engineering Version

According to one embodiment, features may be pre-determined. For example, a model may be constructed by assuming the only features will be the P, Q, R, S, T, and U, features described above. In this case, computational techniques may be used to determine characteristic values (p, q, r, s, t, u) for each of the pre-determined features, as described above. Once the characteristic values have been determined, machine learning techniques may be used to build the model, as described above. For clarity of discussion, this embodiment may be referred to as the engineering version of the method.

B. Deep Learning Version

According to a further embodiment, the features themselves may be identified during the training process. The distinction from A (engineering version) is in the manner in which the features are determined. Here the feature set is not pre-determined, but is determined automatically during the training process. As an example of this scenario, the raw signal (or some appropriately pre-processed version of it) is fed through a deep learning network, which has been trained during the training process to both calculate an optimal feature set, and then to utilize this set to determine the fluid responsiveness index.

According to an embodiment, a method (i.e., algorithm) may be defined to lie somewhere between methods A and B, above. In other words, one may consider a neural network, for example a recurrent neural network (RNN), that acts on the initial raw ECG signal, and converts that raw ECG signal to generate "learned" features. The learned features may then be combined, for example by concatenation, into a larger object (e.g., a vector or a tensor) that includes both learned and engineered features. The larger object may then be used as input to a neural network that outputs a set of classes, in the case of (multi-task) classification, or a set of real numbers, in the class of (multi-task) regression. In further embodiments, other bio-signals may be used to characterize fluid responsiveness instead of, or in addition to ECG signals. In further embodiments, other features may be defined in addition to, or instead of, peak heights and areas under the curve corresponding to feature peaks. Such features may include (but are not limited to):

the raw sampled high-frequency (e.g. 1000 Hz) ECG signal itself;

Fourier or wavelet components calculated from the raw signal;

derivatives or integrals (of any order) computed from the ECG signal, or parts thereof;

Fourier or wavelet components for the derivatives;

features derived from the ECG signal described in above;

any of the above for an arbitrary sequence of cardiac cycles;

differences between any of the above (as well as higher order changes) for different, possibly sequential, cardiac cycles; and different wave (p, QRS) distances, increase and decreases of the angles of the beginning of the curve, etc.

Such features may be determined by the model, rather than engineered explicitly, for example, using modern neural network approaches including (but not limited to): multi-layer perceptrons, deep convolutional neural networks, recurrent neural networks, restricted Boltzmann machines, etc.

Features may also be obtained automatically during a subsidiary unsupervised learning. Machine learning methods may include (but not limited to) k-means clustering, mixture of Gaussians, factor or principal components analysis, deep (variational) autoencoders, or deep generative models. The input to the above subsidiary models may be any set of hand engineered features, including the raw ECG signal itself. These automatically obtained features may then be utilized as part of the main training process in order to determine the fluid responsiveness.

As described above, machine learning models may be generated based on a training process. The training process may be based on a training dataset of ECG signals for which the fluid responsiveness prediction has been measured. For example, measurements may be made on human subjects or during experiments using animals. For example, ECG signals may be measured for animal test subjects including, swine, sheep, etc.

In this regard, animal subjects may be used to determine correlations between measured ECG signals and fluid responsiveness. For example, fluid levels may be increased (e.g., through fluid loading) or decreased (e.g., through bleeding) on animal subjects (e.g., performed on swine or sheep). Data may also be gathered on human subjects undergoing anesthesia. Trends based on animal subjects may then be correlated to trends based on human subjects using Bland-Altman plotting/correlation techniques. With animal subjects, data sets may be gathered during experiments in which a certain fluid volume is changed in a predetermined way (i.e., using bleeding or fluid loading) during the experiment. Such data sets may be well suited to be used as training data sets for machine learning algorithms.

Feature sets calculated from measured ECG signals for training data sets may be referred to as X, while measured outputs (i.e. the measured fluid responsiveness) may be referred to as Y. The machine learning model determines correlations between X and Y. The output Y may consist of a set of classes, in the case of (multi-task) classification, or a set of real numbers, in the class of (multi-task) regression. According to an embodiment, training of a machine learning model may proceed via a supervised learning algorithm, and the model architecture may include (but is not limited to):

a discriminative learning algorithm, such as: linear regression (possibly using kernel methods), a neural network algorithm, for example a multi-layer perceptron, deep convolutional neural network, recurrent neural network, restricted Boltzmann machine, or a generative learning algorithm such as mixture models, hidden Markov models, restricted Boltzmann machines, or generative adversarial network.

According to an embodiment, with generative models, the output may be determined via a theoretical model, that is, by a set of theoretical equations that relates the ECG signal to the blood output of the heart. Such a correlation may be based on inclusion of other metrics such as blood pressure variations, an oxymetry curve, or other homeostatic time dependent metrics.

In the case of neural network models, additional optimization (for example Bayesian optimization, or reinforcement learning techniques) may be performed over model hyperparameters, which may include (but are not limited to): a number of hidden layers, layer sizes, choices between recurrent, convolutional, or fully connected layers. The parameters for a particular architecture may be determined using a standard optimization approach that aims to minimize a difference between a predicted output and a measured output Y utilizing an appropriate cost function, such as (but not limited to) a quadratic cost function, cross-entropy, Hellinger distance, or the Kullback-Leibler divergence.

A particular advantage of deep neural network algorithms is that they may bypass a need to engineer complex features such as those described above, but may work well on raw input data, or a simple transformation or course graining thereof, for example Fourier transforms with a frequency cutoff if necessary. In this regard, they are a lot more data agnostic than algorithms used before deep learning algorithms were developed. Deep learning algorithms do not require detailed knowledge of features specific to cardiology, and their performance is often superior to algorithms pre-dating the development of deep learning algorithms. In this sense, a raw ECG signal itself may be used as input, with the neural network determining the optimal features most suitable for generating the desired output (e.g., for determining the fluid responsiveness). For example, a complete ECG curve may be used as input to a model that detects hypoxia by detecting trends in changes of a distance (i.e., time interval) between S and T features of the ECG curve. Such methods may be applied to other applications of cardiac rhythmology. For example, before a pathological heart rhythm appears (e.g. extrasystole, fibrillation, etc.) there may be characteristic changes in the ECG curve. The above-described neural network models may be of use in automated implantable defibrillators.

As described above, discrete classifier models (e.g., classifier models based on deep neural networks), may be used to complement/validate results obtained by other machine learning models (e.g., regression type neural network models). A result of such a discrete classifier model would be a prescription of whether fluid challenge (e.g., increasing PEEP) should be administered to a patient or not. In other circumstances, a discrete classifier model may prescribe a course of action from three or more possible actions. Machine learning techniques that use discrete classifier models may include (but are not limited to): logistic regression, support vector machines, or any of the above-named neural network approaches, but with a discrete output (achieved for example via a softmax layer).

The training data for such classifier models may be classified in terms of various categories. For example, several categories may be assigned to data from situation is which various corresponding doctor decisions were made. Such categorized data may be used as training data for classifier models. In another example embodiment, training data may be obtained by identifying volume depletion via one or more simple measures such as shortly increasing PEEP, by performing a passive leg raising test, or by administering blood when a fluid responsiveness index falls below a certain value.

In this regard, the decision to administer fluid may be made based on when a value of the fluid responsiveness index falls within a first range of values. Further the amount of fluid may be determined based on the value of the fluid responsiveness index within the first range of values. Similarly, a decision to administer medication to the human subject may be made based on when the value of the fluid responsiveness index falls within a second range of values. Further, the dose of medication may be determined based on the value of the fluid responsiveness index within the second range of values Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar systems for loading computer programs or other instructions into the computer or processor.

The term computer or module may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term computer.

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The terms software and firmware are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

What is claimed is:

1. A processor-implemented method of determining fluid responsiveness and of providing treatment to a human subject based on the determined fluid responsiveness, the method comprising:
   continuously measuring, by a sensor, an electrocardiogram signal of a human subject, the electrocardiogram signal having a frequency greater than 250 Hz to about 1000 Hz;
   performing, by a processor, operations of a first machine learning algorithm using the electrocardiogram signal as input to the first machine learning algorithm to continuously determine features of the electrocardiogram signal;
   performing operations of a second machine learning model, using the determined features as input to the second machine learning model, to generate a fluid responsiveness index as output of the second machine learning model, wherein one of the determined features used as input by the second machine learning algorithm to generate a fluid responsiveness index is a rise angle of the QRS complex of the electrocardiogram signal; and
   administering a course of treatment to the human subject based on the fluid responsiveness index.

2. The method of claim 1, wherein determining features of the electrocardiogram signal comprises:
   determining, by the processor, characteristic values for each of a plurality of pre-determined features of the electrocardiogram signal,
   wherein characteristic values represent one or more of length, amplitude, slope, area, depth, and height, of the pre-determined features.

3. The method of claim 2, wherein the pre-determined features include one or more of the P, Q, R, S, T, and U complex of the electrocardiogram signal.

4. The method of claim 1, wherein performing operations of a first machine learning algorithm comprises performing operations of a neural network algorithm to determine the features.

5. The method of claim 1, wherein performing operations of a first machine learning algorithm comprises performing operations of an unsupervised learning algorithm, wherein the unsupervised learning algorithm comprises a k-means clustering algorithm, a factor or principal components analysis algorithm, a deep (variational) autoencoder algorithm, a deep generative model, or a mixture of Gaussians algorithm.

6. The method of claim 1, wherein the second machine learning model that generates the fluid responsiveness index comprises:
   a discriminative learning algorithm comprising a linear regression algorithm, a neural network algorithm, a multi-layer perceptron, a deep convolutional neural network, a recurrent neural network, or a restricted Boltzmann machine.

7. The method of claim 1, wherein the second machine learning model that generates the fluid responsiveness index comprises:
   a generative learning algorithm comprising a mixture model, a hidden Markov model, a restricted Boltzmann machine, or a generative adversarial network.

8. The method of claim 1, further comprising:
   generating, by the processor, the second machine learning model that generates the fluid responsiveness index by performing a training process comprising:
      receiving a plurality of (X, Y) training data sets, X representing features of a measured ECG signal for a human subject, and Y representing measured fluid responsiveness of the human subject having the measured ECG signal;
      determining correlations between X and Y for the plurality of (X, Y) data sets;
      representing the correlations between X and Y as a mathematical relation; and
      generating the fluid responsiveness index as output Y* of the second machine learning model according to the determined mathematical relation based on the determined input features X*.

9. The method of claim 8, wherein:
   the second machine learning model is a regression model and the determined mathematical relation is an equation that expresses Y as a function of X; or the second machine learning model is a classifier model and the mathematical relation is a partitioning of the multi-dimensional (X, Y) space into two or more regions representing two or more respective classes of Y values as a function of X.

10. The method of claim 1, wherein administering a course of treatment to the human subject based on the fluid responsiveness index comprises:
    administering fluid to the human subject when a value of the fluid responsiveness index falls within a first range of values, wherein the amount of fluid is determined based on the value of the fluid responsiveness index within the first range of values; or
    administering medication to the human subject when the value of the fluid responsiveness index falls within a second range of values, wherein the dose of medication is determined based on the value of the fluid responsiveness index within the second range of values.

11. A system that determines fluid responsiveness and determines a course of treatment for a human subject based on the determined fluid responsiveness, the system comprising:
    a sensor that is configured to continuously measure an electrocardiogram signal of a human subject, the electrocardiogram signal having a frequency greater than 250 Hz to about 1000 Hz;
    a processor that is configured to continuously perform operations comprising:
       receiving the measured electrocardiogram signal of a human subject;

performing operations of a first machine learning algorithm using the electrocardiogram signal as input to determine features of the electrocardiogram signal;

performing operations of a second machine learning model, using the determined features as input to the second machine learning model, to generate a fluid responsiveness index as output of the second machine learning model, wherein one of the determined features used as input by the second machine learning algorithm to generate a fluid responsiveness index is a rise angle of the QRS complex of the electrocardiogram signal; and determining a course of treatment to be administered to the human subject based on the fluid responsiveness index.

12. The system of claim 11, wherein the processor is further configured to determine features of the electrocardiogram signal by performing operations comprising:

determining characteristic values for each of a plurality of pre-determined features of the electrocardiogram signal, wherein characteristic values represent one or more of length, amplitude, slope, area, depth, and height, of the pre-determined features.

13. The system of claim 12, wherein the processor is further configured to determine characteristic values of pre-determined features including one or more of the P, Q, R, S, T, and U complex of the electrocardiogram signal.

14. The system of claim 11, wherein performing operations of a first machine learning algorithm comprises:

performing operations of a neural network algorithm; or performing operations of an unsupervised learning algorithm, wherein the unsupervised learning algorithm comprises a k-means clustering algorithm, a factor or principal components analysis algorithm, a deep (variational) autoencoder algorithm, a deep generative model, or a mixture of Gaussians algorithm.

15. The system of claim 11, wherein the processor is further configured to generate the fluid responsiveness index by performing operations of a discriminative learning algorithm, wherein the discriminative learning algorithm comprises:

a linear regression algorithm;

a neural network algorithm;

a multi-layer perceptron;

a deep convolutional neural network;

a recurrent neural network; or a restricted Boltzmann machine.

16. The system of claim 11, wherein the processor is further configured to generate the fluid responsiveness index by performing operations of a generative learning algorithm, wherein the generative learning algorithm comprises:

a mixture model;

a hidden Markov model;

a restricted Boltzmann machine; or a generative adversarial network.

17. The system of claim 11, wherein the processor is further configured to generate the second machine learning model that generates the fluid responsiveness index by performing a training process comprising:

receiving a plurality of (X, Y) training data sets, X representing features of a measured ECG signal for a human subject, and Y representing measured fluid responsiveness of the human subject having the measured ECG signal;

determining correlations between X and Y for the plurality of (X, Y) data sets;

representing the correlations between X and Y as a mathematical relation; and generating the fluid responsiveness index as output Y* of the machine learning model according to the determined mathematical relation based on the determined input features X*, wherein:

the machine learning model is a regression model and the determined mathematical relation is an equation that expresses Y as a function of X; or the machine learning model is a classifier model and the mathematical relation is a partitioning of the multi-dimensional (X, Y) space into two or more regions representing two or more respective classes of Y values as a function of X.

18. The system of claim 11, wherein the processor is further configured to determine the course of treatment to be administered to the human subject based on the fluid responsiveness index by performing operations comprising:

determining that fluid should be administered to the human subject when a value of the fluid responsiveness index falls within a first range of values, and determining the amount of fluid to be administered based on the value of the fluid responsiveness index within the first range of values; or determining that medication should be administered to the human subject when the value of the fluid responsiveness index falls within a second range of values, and determining the dose of medication based on the value of the fluid responsiveness index within the second range of values.

* * * * *